United States Patent [19]

Dewey et al.

[11] Patent Number: 5,558,666

[45] Date of Patent: Sep. 24, 1996

[54] HANDPIECE FOR PRODUCING HIGHLY COLLIMATED LASER BEAM FOR DERMATOLOGICAL PROCEDURES

[75] Inventors: David A. Dewey, Sunnyvale; Michael Arnett, Los Altos Hills; Dale E. Koop, Sunnyvale; David Trost, San Francisco, all of Calif.

[73] Assignee: Coherent, Inc., Santa Clara, Calif.

[21] Appl. No.: 183,111

[22] Filed: Jan. 14, 1994

[51] Int. Cl.⁶ .................................................. A61N 5/06
[52] U.S. Cl. .......................... 606/9; 606/10; 606/13
[58] Field of Search ...................... 606/2–19; 607/89–93

[56] References Cited

U.S. PATENT DOCUMENTS

| | | | |
|---|---|---|---|
| 3,547,125 | 12/1970 | Tagnon | 606/4 |
| 3,703,176 | 11/1972 | Vassiliadis et al. | 606/4 |
| 3,982,541 | 9/1976 | L'Esperance, Jr. | 606/4 |
| 4,211,229 | 7/1980 | Wurster . | |
| 4,388,924 | 6/1983 | Weissman et al. | 606/9 |
| 4,473,074 | 9/1984 | Vassiliadis | 606/19 |

FOREIGN PATENT DOCUMENTS

| | | | |
|---|---|---|---|
| 152686 | 8/1985 | European Pat. Off. | 606/17 |
| 0274205A3 | 7/1988 | European Pat. Off. | A61F 9/00 |
| 0511805A3 | 11/1992 | European Pat. Off. . | |
| 2170616 | 8/1986 | United Kingdom . | |

*Primary Examiner*—David M. Shay
*Attorney, Agent, or Firm*—Limbach & Limbach L.L.P.

[57] ABSTRACT

A handpiece for use in delivering the output beam of a laser to the surface of a patient's skin for performing a dermatological procedure. In a first and second embodiment of the present invention, the handpiece provides a highly collimated beam of a fixed, non-variable spot size which is largely insensitive to movement of the handpiece over a range of working positions. In a third embodiment the handpiece provides a highly collimated and well defined focused laser spot of variable size where for a selected spot size, the size is largely insensitive to movement of the handpiece over a range of working positions. In all of the embodiments, the highly collimated laser beam permits the surgeon performing the procedure to move the handpiece over a range of positions without significantly defocusing or altering the spot size of the beam.

10 Claims, 7 Drawing Sheets

HANDPIECE FOR PRODUCING HIGHLY COLLIMATED LASER BEAM FOR DERMATOLOGICAL PROCEDURES

TECHNICAL FIELD

The present invention is generally directed to lasers used for dermatological procedures, and more specifically, to a handpiece which is used to direct the output of a laser to the surface of a patient's skin and produces a highly collimated beam having a diameter which is largely insensitive to movements of the handpiece over a range of working positions.

BACKGROUND OF THE INVENTION

Lasers are commonly used today for a variety of medical applications. One of these applications is to perform dermatological procedures, such as removal of foreign pigments in the skin (tattoos), treatment of vascular disorders which cause unwanted pigmentation ("wine marks"), and to destroy skin tumors by ablating the affected tissue.

In most dermatological applications, a handpiece is used to guide the output of the laser to the patient's skin and to form a laser spot of a desired size on the region of the skin which is to be treated. The handpiece is typically attached to one end of an articulated arm which transmits the output of a medical laser (such as a $CO_2$ laser for many dermatological applications) to the handpiece and allows the handpiece to have a wide range of motion.

Prior art dermatological handpieces rely on a parfocal optical system to bring the laser beam to a focus. One such optical system is a zoom lens system which is contained in a dermatology handpiece for Argon lasers manufactured by Nidek of Tokyo, Japan. This zoom system is coupled to an optical fiber at one end and to an Argon laser at the other end. In such a system an image of the end of the optical fiber is relayed to the work area, thereby producing a well defined laser spot. Coherent, Inc. of Palo, Alto, Calif., the assignee of the present invention, produces a dermatology handpiece for use with $CO_2$ lasers. This handpiece is not coupled to an optical fiber because present fibers do not have sufficient transmissivity at the wavelength of the laser beam produced by $CO_2$ lasers. The laser spot produced by this handpiece has an intensity which decreases as a function of the distance from the beam center, owing to the Gaussian nature of the output beam.

It is desireable that the laser beam be in focus at the skin surface so that little heat transfer or ablation occurs outside of the desired treatment area and at locations beneath the skin surface. It is also desireable that the beam be highly collimated, that is composed of substantially parallel rays of light, so that the overall laser beam diverges very little over a working region in front of the skin surface. This characteristic reduces collateral damage to the areas surrounding the work area and makes it easier for the surgeon to perform the procedure since the size of the laser spot is less sensitive to small movements of the handpiece.

The energy density of a pulsed laser beam which is delivered to a patient's tissue depends on the area of the beam at the tissue surface and the energy content of the pulse. The area of the laser beam at the tissue surface is proportional to the square of the spot size, which is determined by the spot diameter. Thus, if the spot size changes as the surgeon moves the handpiece over a range of working positions, the energy density can be changed to an even greater degree. This can lead to difficulties in properly completing the procedure. A highly collimated beam thus insures that under practical working conditions, the energy density of the laser beam delivered to the working area is determined by the surgeon's selection of the pulse energy for the laser pulses and not by the movements of the handpiece.

Prior art handpieces such as the Nidek system referred to above are capable of delivering a beam having a range of spot sizes, however, each spot size is in focus within only a very limited range of distances from the end of the handpiece. Thus, the laser beam produced by this system is not highly collimated. Similarly, the beam produced by the Coherent handpiece is also not highly collimated. This feature means that the surgeon has to maintain an approximately constant distance between the end of the handpiece and the target tissue in order to safely and effectively perform the procedure.

Figure 1:
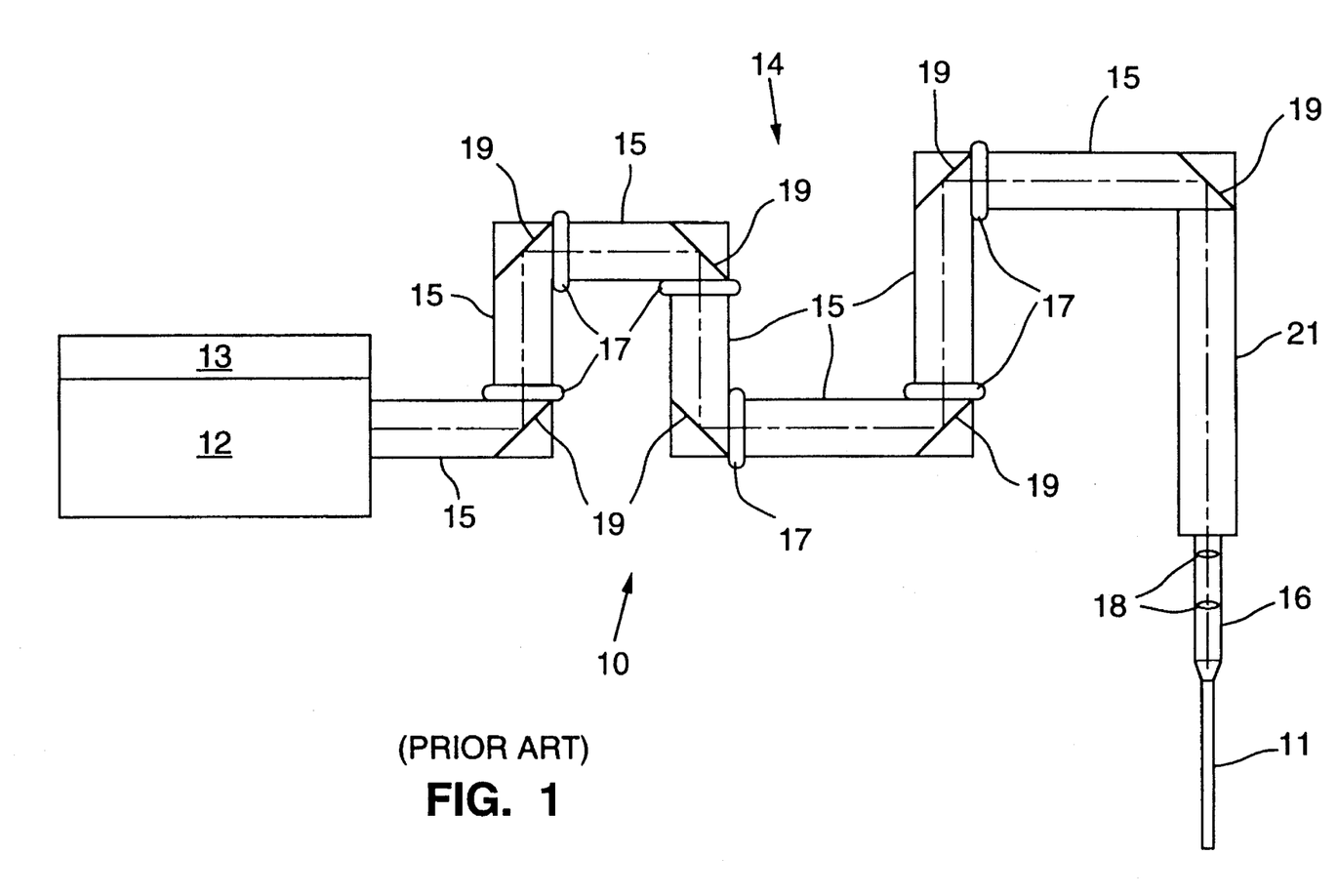
FIG. 1 shows the primary components of a prior art laser system capable of delivering a laser spot to a desired region of a patient's skin.

FIG. 1 shows the primary components of a prior art laser system suitable 10 for delivering a laser spot to a desired region of a patient's skin. Laser system 10 includes a laser source 12 which produces a laser beam at its output and an articulated arm 14 which relays the beam to a handpiece 16, through which a beam 11 exits and propagates to the surface of a patient's skin.

Articulated arm 14 is composed of multiple successive straight segments 15 interconnected by rotatable joints 17. Each rotatable joint 17 is associated with a mirror 19. A laser beam entering each segment 15 of articulated arm 14 is redirected down the subsequent segment 15 by the mirror 19 associated with each rotatable joint 17. The rotatable joints 17 are able to rotate while maintaining beam alignment down each successive segment 15 so that delivery segment 21 can direct the beam to a target location at a desired angle. Delivery segment 21 directs the beam out of articulated arm 14 to either the target tissue or another delivery system, such as handpiece 16. Handpiece 16 usually contains an optical system 18 which acts to focus the beam, producing beam 11 which propagates to the patient's skin.

In addition to the mentioned elements, laser system 10 also usually includes a pointing laser 13 which produces a pointing spot which is co-linear with the output beam of laser 12 after its propagation through arm 14 and handpiece 16. The pointing spot assists the surgeon to correctly position the medical laser beam on the patient's skin.

Optical system 18 is capable of delivering laser energy in the form of a clearly focused spot to the surface of a patient's skin. In some systems, the spot size may be varied in diameter, however in typical prior art systems, the spot size selected will remain in focus only if handpiece 16 is confined to motion over a very limited range of distances around the position at which the spot is properly focused. This requires the surgeon performing the procedure to maintain a constant (or nearly constant) distance between the end of the handpiece and the skin surface. Under actual operational conditions this requirement is sometimes difficult to satisfy and places an additional constraint on the surgeon which can impact their ability to effectively carry out the procedure.

What is desired is a laser handpiece for use in dermatological applications which is capable of delivering a well defined, focused laser spot to the surface of a patient's skin, where the spot size is largely insensitive to movement of the handpiece over a range of working positions. It is also desired to have a handpiece which is capable of producing a variety of spot sizes, where each selected spot size is largely insensitive to movement of the handpiece over a range of working positions.

SUMMARY OF THE INVENTION

The present invention is directed to a handpiece for use in delivering laser radiation to the surface of a patient's skin during a dermatological procedure. The handpiece provides a highly collimated beam having a well defined, focused laser spot the size of which is largely insensitive to motions of the handpiece over a range of working positions. This permits the surgeon to move the handpiece over the range of positions without significantly altering the spot size.

In the preferred embodiment of the invention, the dermatology handpiece is intended to be used to deliver laser radiation from a $CO_2$ laser to the skin surface. In first and second embodiments of the present invention, the handpiece includes an optical system composed of two elements, typically a two lens telescope, which focuses the beam onto the surface of a patient's skin. The telescope alters the diameter of the laser beam from its size exiting the laser and produces a highly collimated beam having a fixed spot size which is largely insensitive to movement of the handpiece over a range of working positions. An aperture may be added prior to the first element of the optical system to alter the Gaussian profile of the fundamental mode of $CO_2$ lasers typically used for dermatological applications and impose a more uniform intensity profile on the highly collimated beam produced by the telescope.

In a third embodiment of the handpiece of the present invention, the optical system includes three optical elements, typically lenses, which form a zoom lens system capable of focusing a beam waist at a small range of locations from the end of the handpiece. The waist formed by the zoom lens system can be varied in size, and for each size the system is able to maintain substantially the same size and energy distribution of the spot over the range of working positions. In this embodiment an aperture may also be used prior to the first optical element to assist in producing a highly collimated beam having a substantially uniform intensity profile.

If an aperture is used as part of the present invention, the diffraction effects of the aperture produce a sharper fall off of intensity at the beam edge than occurs in the case of an un-apertured beam. The maximum edge sharpness is achieved when the aperture is positioned so that an image of the aperture is projected onto the patient's skin.

Further objects and advantages of the present invention will become apparent from the following detailed description and accompanying drawings.

DESCRIPTION OF THE PREFERRED EMBODIMENT

Figure 2A:
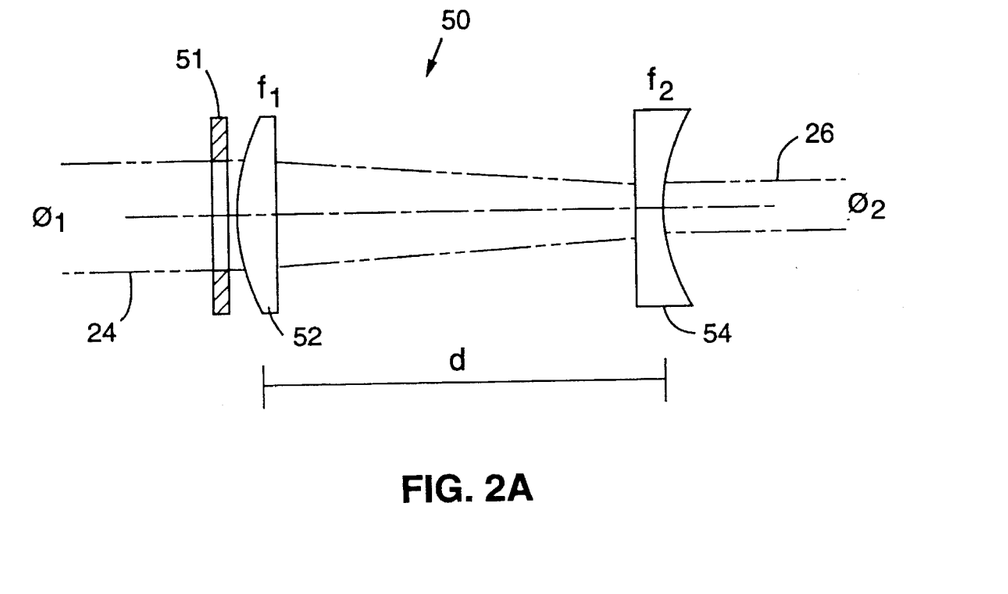
FIGS. 2A–2B show the components of the optical system of a first and second embodiment of the laser handpiece of the present invention.
Figure 2B:
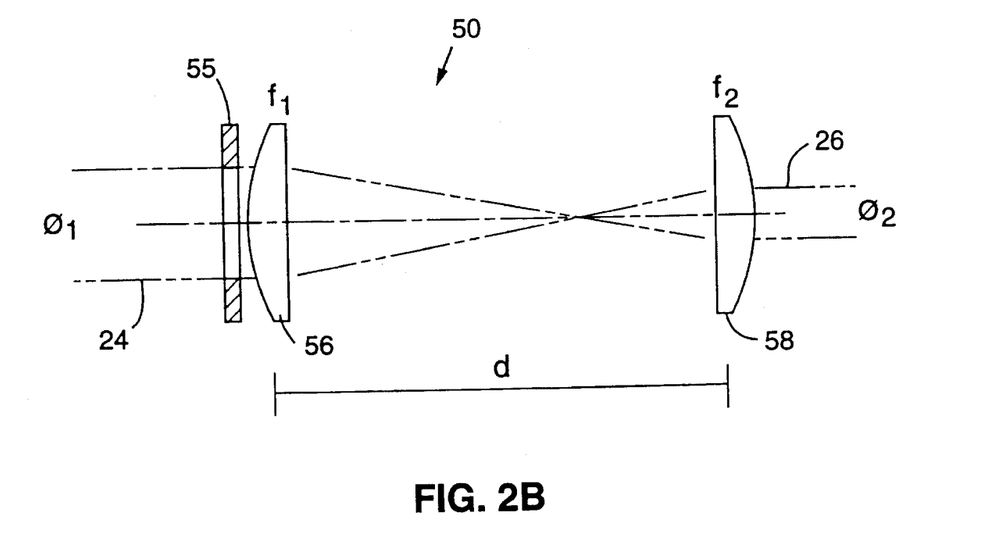

Referring to the figures, and in particular to FIGS. 2A–2B, which show the components of an optical system 50 of a first (FIG. 2A) and a second (FIG. 2B) embodiment of the laser handpiece of the present invention. Optical system 50 acts to transform a laser beam 24 which is the output of a $CO_2$ or other suitable laser (not shown) into a highly collimated beam 26 which is intended to be used for a dermatological procedure. In FIG. 2A, optical system 50 includes a two element telescope which includes fixed position lenses 52 and 54. Lenses 52 and 54 act to produce an output beam 26 which is highly collimated but of a fixed spot size.

As depicted in FIG. 2A, lens 52 is a converging lens while lens 54 is a diverging lens which acts to focus and collimate the beam. The effect of optical system 50 is to produce a highly collimated beam having a diameter which is smaller than the initial laser beam. An aperture 51 may be placed in front of lens 52 to alter the inherently Gaussian beam profile of the output of $CO_2$ lasers which are typically used for dermatological procedures into one which has a sharper edged profile over the range of working distances. The beam coming out of aperture 51 also has a more uniform intensity profile (and hence more uniform energy distribution across the beam diameter) than does the beam coming directly out of the laser. In the preferred embodiment, aperture 51 has a circular cross section and a diameter of 6.00 mm.

FIG. 2B shows another embodiment of a two lens configuration which can be used to produce a highly collimated beam having a diameter which is smaller than the initial laser beam. In FIG. 2B, lens 56 and lens 58 are converging lenses with lens 58 being placed beyond the focal point of lens 56. As with the embodiment of the present invention shown in FIG. 2A, an aperture 55 may be placed in front of lens 56 to alter the profile of beam 24 coming out of the laser. In addition to the configurations shown in FIGS. 2A–2B, other types of optical elements may be used, such as spherical or parabolic mirrors, and are intended to be included within the description of the invention contained in this application. The use of such other elements is well known to those skilled in the art.

In general, the optical elements included in optical system 50 must satisfy the parametric equations given below, where $\phi_1$ is the initial beam diameter, $\phi_2$ is the final beam diameter, $f_1$ is the focal length of the first lens, $f_2$ is the focal length of the second lens, and d is the separation of the lenses:

$$|f_1/f_2|=\phi_1/\phi_2; \text{ and} \qquad (1)$$

$$f_1+f_2=d. \qquad (2)$$

For the optical system design shown in FIG. 2A, the parameter values are:
$f_1=+50$ mm;
$f_2=-25$ mm;
$d=25$ mm;
$\phi_1=6$ mm; and
$\phi_2=3$ mm.

When used with a $CO_2$ laser having a wavelength of 10.6 μm, ZnSe or ZnS are the preferred lens materials. The lens surfaces can be coated with anti-reflective coatings to minimize power losses. If a pointing beam such as that produced by a HeNe laser is used, the lenses should be centered and the pointing beam should be coaxial with the $CO_2$ laser beam. Another option is to use optical elements having diffractive surfaces so that there is minimal dispersion between the pointing beam and the treatment beam. If mirror optical elements are used, little dispersion occurs, however, aberrations may be produced if the mirrors are tilted. Aberrations can be reduced by using off-axis aspheric mirror optical elements instead of centered or on-axis ones.

Optical system 50 of FIGS. 2A–2B provides the benefits of a highly collimated beam in a device which is simple and inexpensive to construct. A handpiece which includes optical system 50 is useful for dermatological applications such as skin resurfacing where a variable spot size is not needed or as useful. The $CO_2$ laser with which the handpiece containing optical system 50 is intended to be used is the Ultrapulse™ $CO_2$ laser manufactured by Coherent, Inc. The Ultrapulse™ laser has an output beam having a diameter of approximately 6.25 mm which is reduced to a diameter of 3 mm by the action of optical system 50 (as depicted in FIG. 2A) when it is designed according to the parameter values given above.

Figure 3:
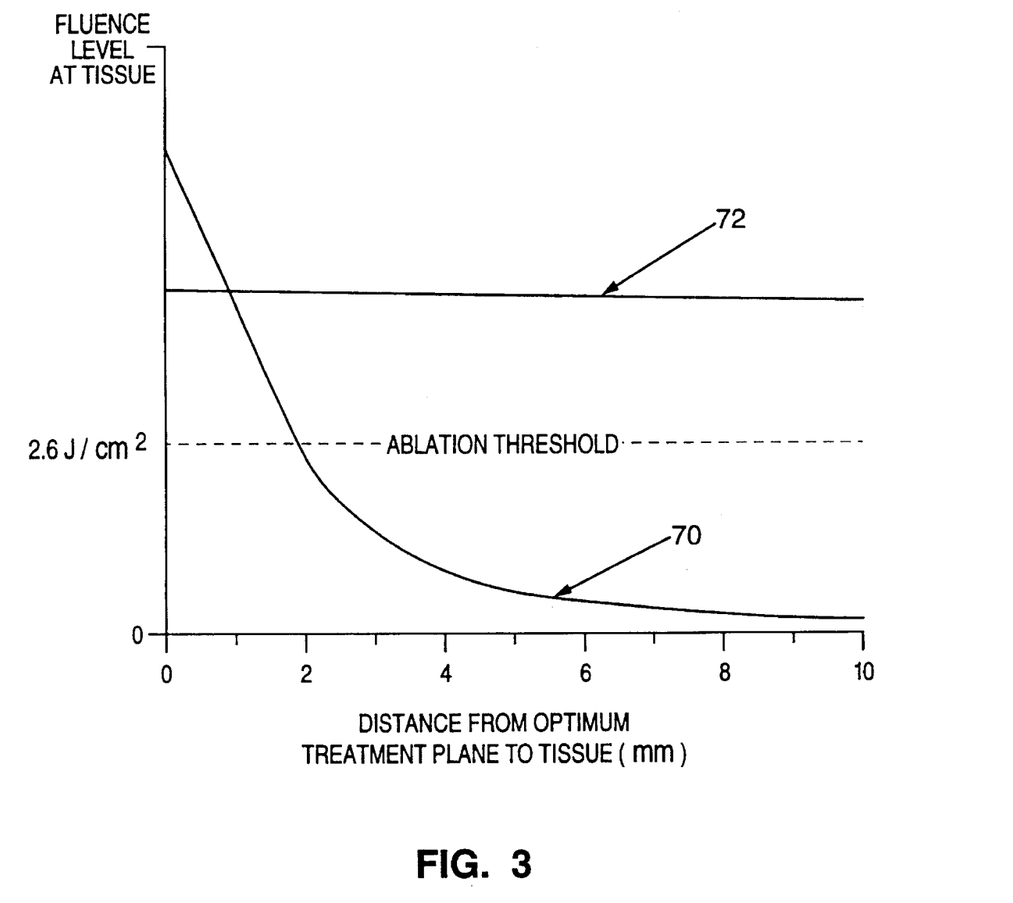
FIG. 3 is a graph showing the fluence level of a laser spot projected onto a patient's skin as a function of the distance between the optimum treatment position of a handpiece and the skin for a prior art handpiece which does not produce a highly collimated beam and for the handpiece of FIG. 2A.

FIG. 3 is a graph showing the fluence level (energy per unit area) of a laser spot projected onto a patient's skin as a function of the distance between the optimum treatment position of a handpiece and the skin for a prior art handpiece which does not produce a highly collimated beam and for the handpiece of FIG. 2A. As the curves in FIG. 3 indicate, the fluence level 70 of a prior art handpiece which does not produce a highly collimated beam varies significantly over the range of working positions shown in the figure. This means that for small variations in the position of the handpiece, the energy density of the laser beam delivered to the patient's skin may vary enough to cause it to be insufficient to carry out the intended procedure. In contrast, the fluence level 72 produced by the optical system 50 of the embodiment of the present invention shown in FIG. 2A is substantially constant over the range of working positions and thus is less sensitive to movements of the handpiece.

As an indication of the highly collimated beam realized by the present invention, the beam diameter of the beam produced by a handpiece incorporating the optical system of FIG. 2A has been determined as a function of distance in front of the handpiece. The results are shown in the table below, where "Position" refers to the distance (mm) in front of the location of the first surface of lens 52 at which the beam size was determined and "Radius" refers to the beam radius (in mm) at that position:

| Position | Radius |
|---|---|
| 50 mm | 1.504 mm |
| 60 mm | 1.507 mm |
| 70 mm | 1.510 mm |
| 80 mm | 1.513 mm |
| 90 mm | 1.517 mm |
| 100 mm | 1.521 mm |
| 110 mm | 1.526 mm |
| 120 mm | 1.531 mm |
| 130 mm | 1.537 mm |
| 140 mm | 1.543 mm |
| 150 mm | 1.549 mm |
| 160 mm | 1.556 mm |
| 170 mm | 1.564 mm |
| 180 mm | 1.572 mm |
| 190 mm | 1.580 mm |
| 200 mm | 1.589 mm |
| 210 mm | 1.598 mm |
| 220 mm | 1.608 mm |

Figure 4:
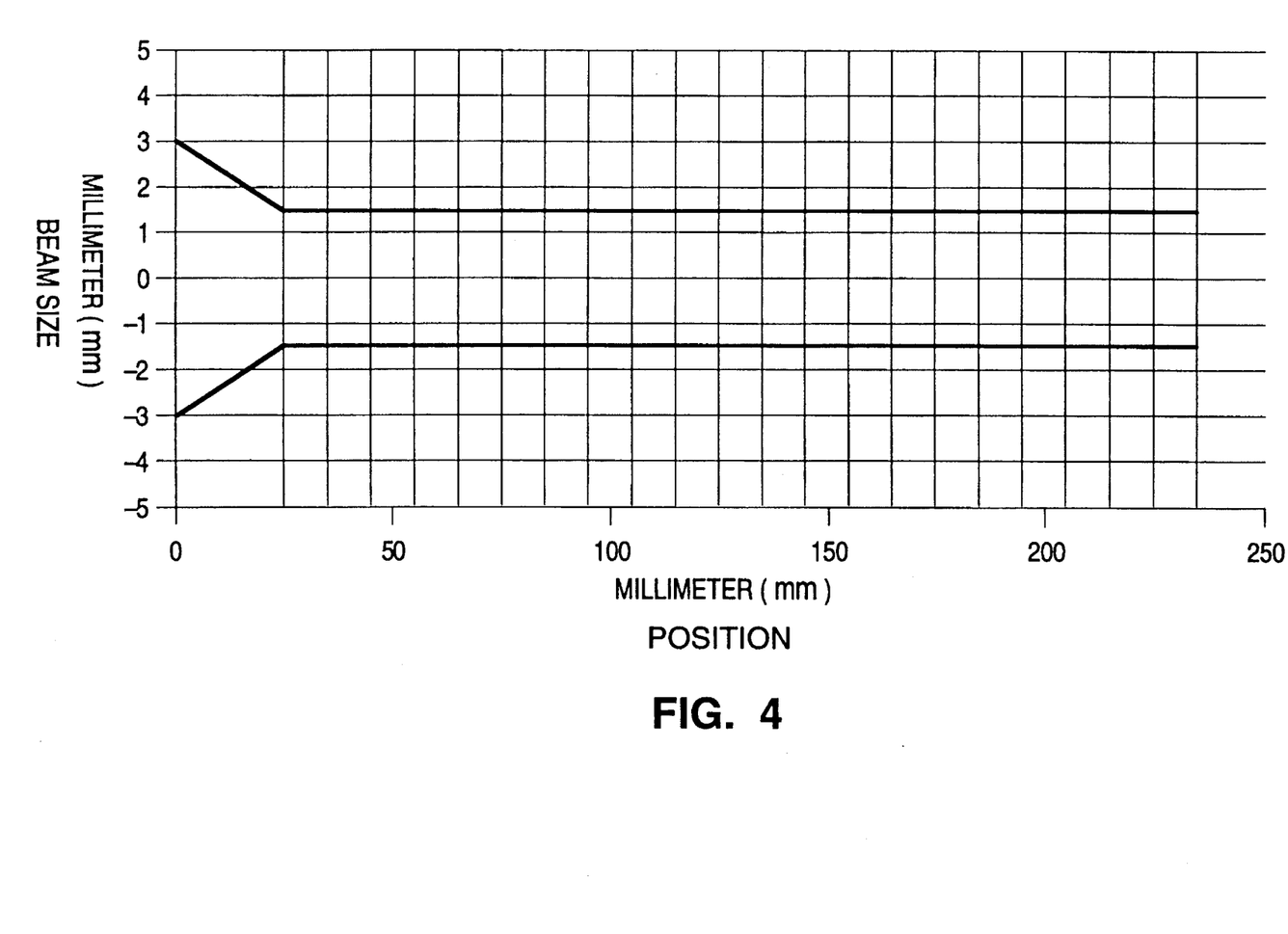
FIG. 4 shows the beam size as a function of position in front of the handpiece for the optical system of FIG. 2A.

The data in the above table is plotted in FIG. 4, which shows the beam size as a function of position in front of the handpiece for the optical system of FIG. 2A. As indicated by the data in the table, the 3 mm diameter spot produced by the action of lenses 52 and 54 varies from a diameter of 3.042 mm to 3.216 mm over the range of 100 mm to 220 mm in front of the first surface of lens 52. This represents a diameter variation of approximately 6% over that range of working positions. Note that the above data was obtained for the case in which aperture 51 was not used.

Figure 5:
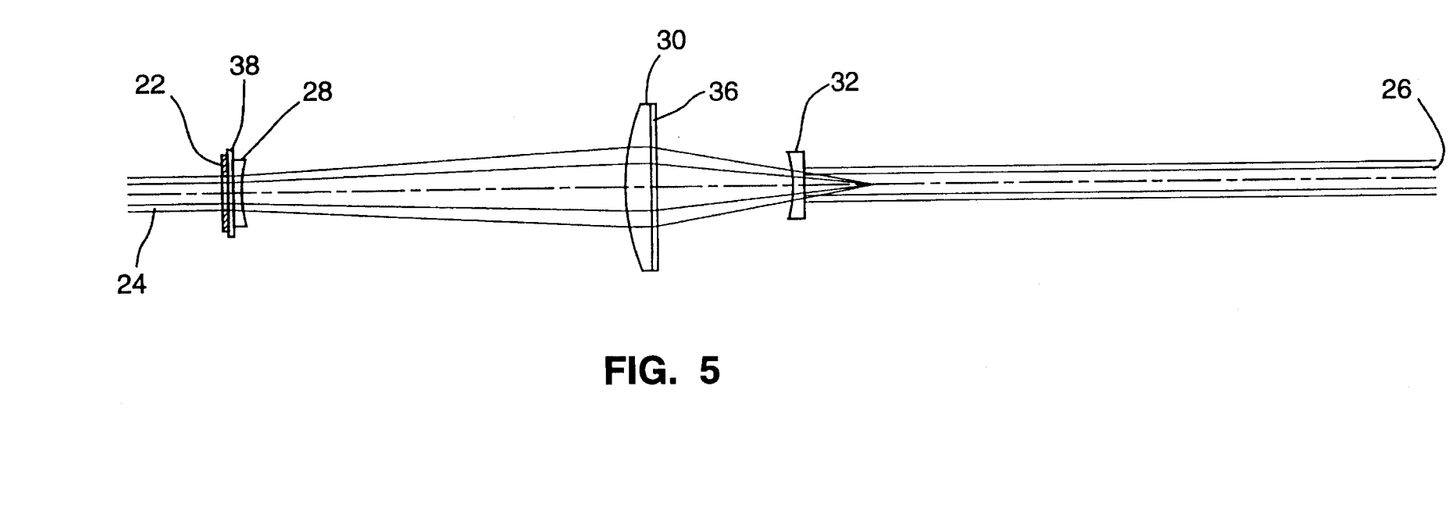
FIG. 5 shows the components of the optical system of a third embodiment of the laser handpiece of the present invention.

FIG. 5 shows the components of an optical system 20 of a third embodiment of a laser handpiece of the present invention. Optical system 20 again acts to transform a laser beam 24 into a highly collimated beam 26 which is suitable for use in dermatological procedures. The first element of optical system 20 is an aperture 22 which, as mentioned above, serves to alter the beam profile of the $CO_2$ laser into one which has a sharper edged profile over the range of working distances. The beam coming out of aperture 22 also has a more uniform intensity profile (and hence more uniform energy distribution across the beam diameter) than does the beam coming directly out of the laser. The diffraction effects of the aperture produce a sharper fall off of intensity at the beam edge than occurs in the case of an unapertured beam. The maximum edge sharpness is achieved when the aperture is positioned so that an image of the aperture is projected onto the patient's skin. In the preferred embodiment, aperture 22 has a circular cross section and a diameter of 6.00 mm. As noted with reference to the embodiments of the present invention depicted in FIGS. 2A–2B, aperture 22 can be removed from optical system 20 and the invention will still provide a highly collimated beam.

After exiting aperture 22 the beam passes through a diverging (negative) lens 28. Lens 28 is located at a fixed position and causes beam 24 to diverge and form a virtual image of the beam waist at a specified location behind lens 28. "Beam waist" refers to the location along the beam profile at which the beam has its smallest cross section. After passing through lens 28, beam 24 passes through a converging (positive) lens 30 which is free to move over a limited range of distances and which relays the image of the beam waist formed by lens 28 to a range of locations in front of lens 30.

After passing through lens 30 beam 24 then passes through a final diverging (negative) lens 32 which re-collimates beam 24 and allows it to exit the handpiece with a spot size diameter which is determined by the positions of movable lenses 30 and 32. Exiting beam 26 has a long depth of focus which enables it to maintain its collimated character over the range of working positions. The positions of lenses 30 and 32 are controlled by a cam which links their movements together so that the position of lens 32 is maintained at approximately one focal length behind the position of the beam waist projected by lens 30. In the preferred embodiment, lenses 28, 30, and 32 are composed of Zinc Selenide (ZnSe) which has an index of refraction of 2.4028 at a wavelength of 10.6 μm, corresponding to the output of the $CO_2$ laser, and 2.5911 at a wavelength of 633 nm, corresponding to the output of the HeNe pointing laser.

As noted, lens 30 relays the waist formed by lens 28 to a range of locations approximately 78 to 104 millimeters from the surface of lens 28. The lens chosen for use in the preferred embodiment nominally has the capability of magnifying the image of the beam waist by a factor of 2.5 at one extreme of the range over which it can travel, and by a factor of 1/2.5 at the other end of its travel. The magnification factor is modified by altering the position of lens 30 at the small spot size positions corresponding to one end of the travel range of lens 30. The position of lens 32 is correspondingly modified away from its location one focal length behind the beam waist to restore the magnification factor while projecting the resulting beam waist to the center of the intended working range. The intended working range refers to the range of positions from the laser output (the location of aperture 22) at which the beam size is intended to remain approximately constant. In the preferred embodiment of the present invention, this range has been selected to be approximately 150 to 250 mm from the location of aperture 22. The position of lens 32 has been adjusted to produce a final beam which remains approximately constant in size over the working range. The positions of lenses 30 and 32 are indicated by the zoom position table which is discussed later in this application.

In accordance with the present invention, the laser handpiece described with reference to FIGS. 2A, 2B, and 5 can be used by a surgeon to perform dermatological procedures on a patient by either directing the laser beam onto one region of the patient's skin, or by scanning the beam over a larger region of the skin. The beam is typically directed onto one region of the skin to ablate skin tumors and is scanned over a larger region to remove pigmentation or resurface the skin in that region.

The handpiece of FIGS. 2A–2B produces a spot of fixed size and is suited for use in skin resurfacing, while the handpiece of FIG. 5 produces a spot of variable size and is suited for applications requiring greater control of the spot size. In any of the embodiments of the present invention disclosed in this application, the optical system of the laser handpiece produces a highly collimated beam so that the spot size varies little if the handpiece is moved over a range of working positions. This enables the surgeon to move the handpiece within the range of positions without significantly reducing the energy density of the spot and hence the effectiveness of the procedure. Thus, the surgeon is able to concentrate on properly performing the procedure and is not distracted by attempting to keep the handpiece at a fixed position in order to maintain a constant sized laser spot on the patient's skin.

Figure 6:
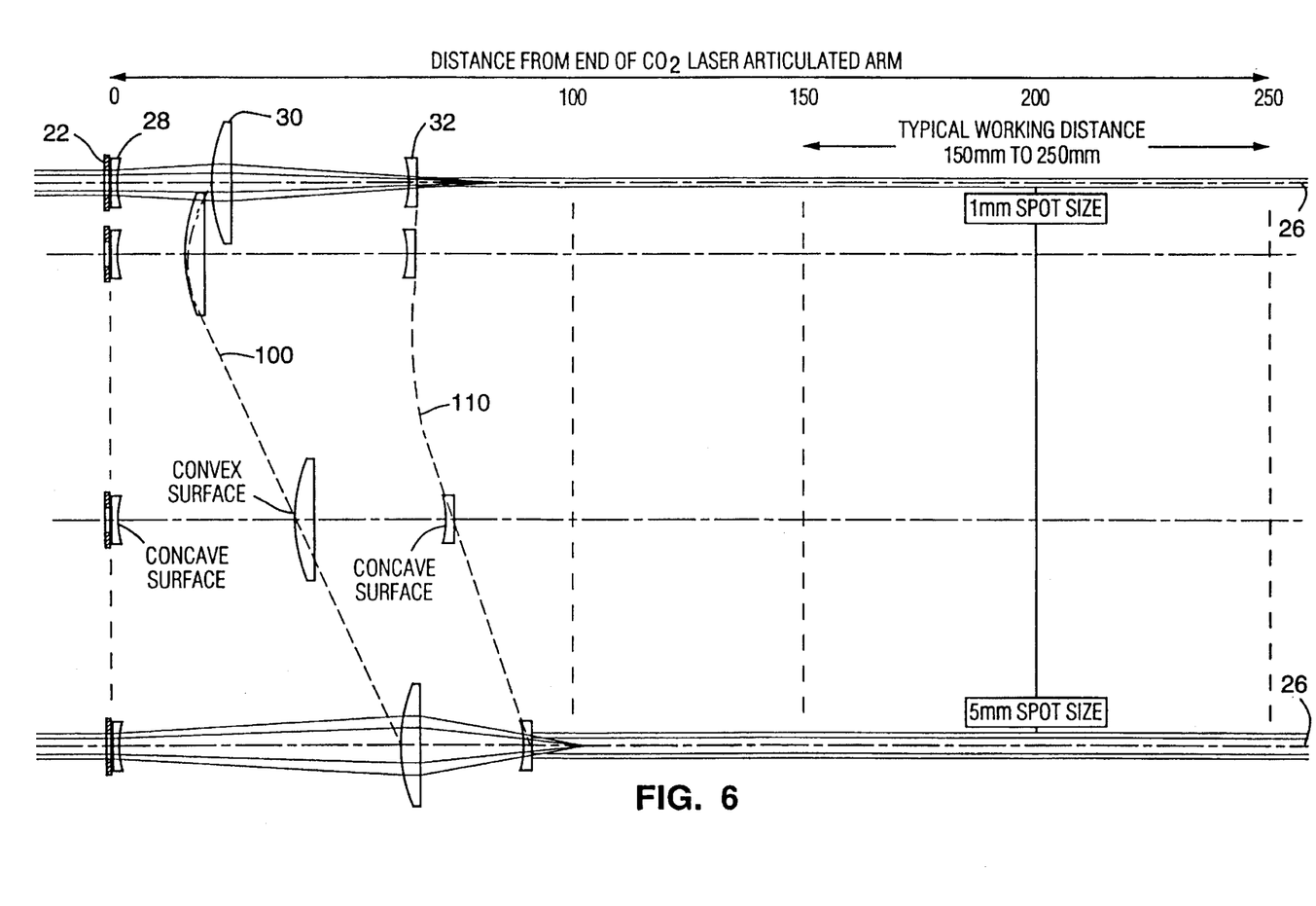
FIG. 6 shows the elements of the optical system of FIG. 5 and indicates the relative positions of the two movable elements of the optical system and the correspondence to the final spot size produced by the system.

FIG. 6 shows the elements of optical system 20 and indicates the relative positions of movable elements 30 and 32 and the correspondence to the final spot size produced by the system. As depicted in FIG. 6, aperture 22 is placed at the origin, as is surface 1 of lens 28. The relative positions of lens 30 and lens 32 as they are moved are indicated by dotted lines 100 and 110, respectively.

In the preferred embodiment, lens 28 has a flat first surface and a curved second surface having a radius of curvature of 55.73 mm. The thickness of lens 28 is 2 mm. Lens 30 has a first surface having a radius of curvature of 39.90 mm, a flat second surface, and a thickness of 4 mm. Lens 32 has a first surface having a radius of curvature of −22.20 mm, a flat second surface, and a thickness of 2 mm. The diameters of lenses 28, 30, and 32 are chosen to be sufficient to encompass the beam width at the location(s) of the lenses while allowing enough additional surface area to enable the lenses to be connected to mounting hardware.

In accordance with the preferred embodiment of the present invention, applying optical system 20 of FIG. 5 to the output of a dermatological laser provides an image of the beam waist at a location which is approximately 200 mm from the location of aperture 22. Output beam 26 is highly collimated and its spot size can be varied by the movement of lenses 30 and 32. The movement of lenses 30 and 32 is controlled by a cam system which is typically constructed so that the spot size varies linearly with cam rotation angle. Thus, lenses 28, 30, and 32 form a mechanically compensated zoom lens system.

The surfaces of the elements of optical system 20 may be fabricated so as to have a diffractive element to correct for the different refractive indices of the lens material at the wavelengths corresponding to the $CO_2$ laser (10.6 μm) and the HeNe pointing laser (633 nm). This enables the $CO_2$ laser spot and HeNe pointing laser spot to remain approximately the same size as the positions of the lenses are varied. The inventors of the present invention have found that placing a diffractive element 38 (shown in FIG. 5) having a 50% correction on the first surface of lens 28 and a diffractive element 36 having a 70% correction on the second surface of lens 30 provides an adequate correction for chromatic aberration without significantly reducing the beam energy.

Figure 7:
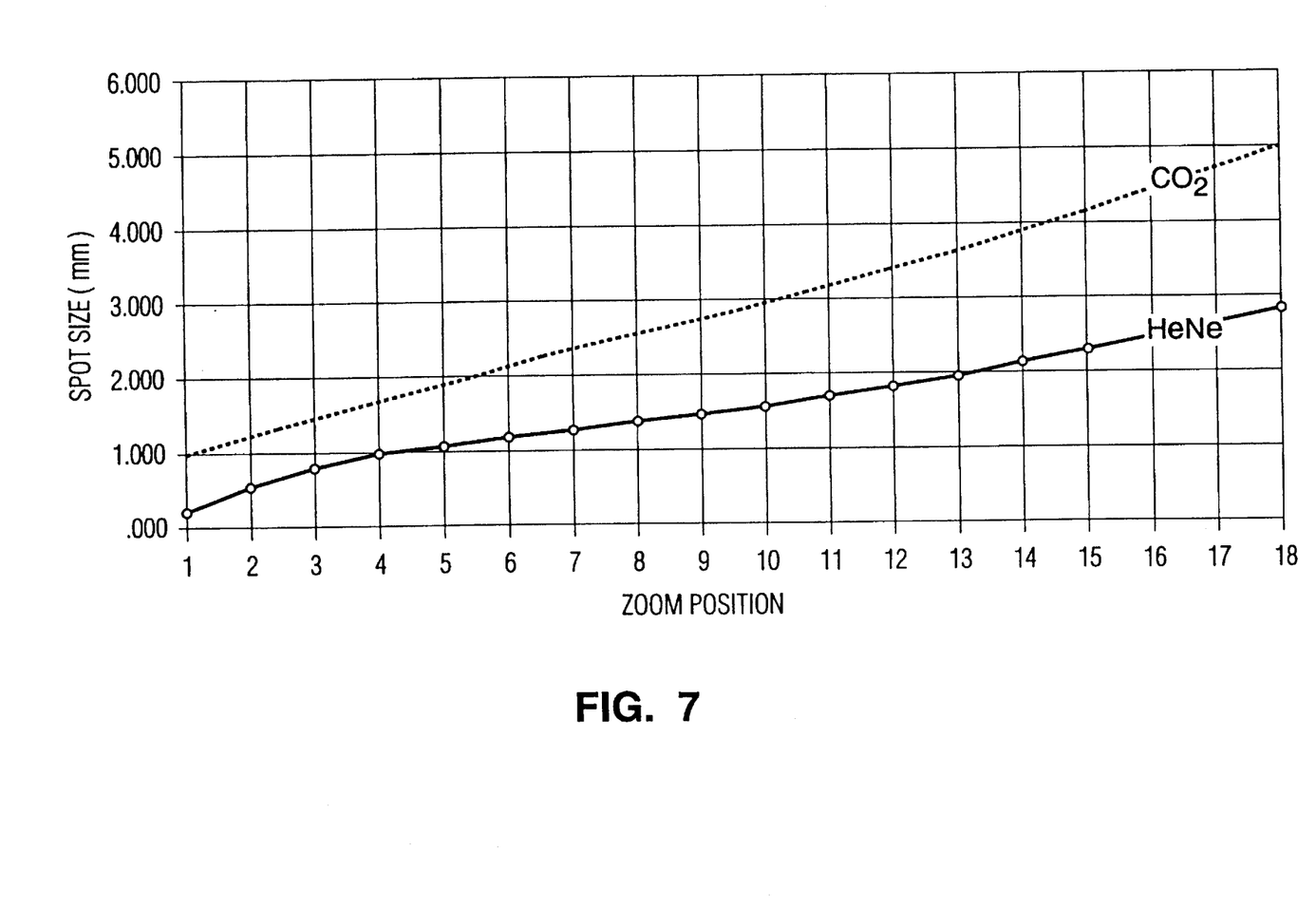
FIG. 7 is a graph showing the spot size (in mm) of the $CO_2$ laser beam and the HeNe pointing laser beam as a function of zoom position for the optical system of FIG. 5.

FIG. 7 is a graph showing the spot sizes (in mm) of the $CO_2$ laser beam and the HeNe pointing laser beam as a function of zoom position for the optical system 20 of FIG. 5. The data depicted in FIG. 7 is based on the use of the partial chromatic aberration correction supplied by diffractive elements 36 and 38. As indicated by FIG. 7, the spot size of the $CO_2$ and HeNe lasers are monotonically related, so that as the $CO_2$ laser spot size increases, the HeNe spot size does also. The spot size of the $CO_2$ laser varies from approximately 1 mm to 5 mm as the positions of the optical elements are changed.

Zoom position refers to the positions of movable optical elements 30 and 32 and is defined according to the table below, where Zoom is the zoom position, SS is the corresponding spot size in mm measured at the center of the range of working positions (approximately 200 mm from the position of the aperture), P1 is the position of the first surface of lens 30 measured in mm from aperture 22, and P2 is the position of the second surface of lens 32:

| Zoom | SS | P1 | P2 | Range | $D_e$ |
| --- | --- | --- | --- | --- | --- |
| 1 | 0.929 | 21.961 | 66.277 | 144.64% | 14.09 |
| 2 | 1.2044 | 17.542 | 65.78 | 122.564% | 10.89 |
| 3 | 1.4233 | 16.241 | 65.704 | 116.604% | 9.29 |
| 4 | 1.6746 | 17.714 | 65.14 | 109.55% | 7.84 |
| 5 | 1.8595 | 19.49 | 64.918 | 106.47% | 7.03 |
| 6 | 2.1183 | 21.961 | 65.016 | 105.104% | 6.18 |
| 7 | 2.3462 | 24.585 | 65.554 | 104.294% | 5.59 |
| 8 | 2.5398 | 27.324 | 66.475 | 102.95% | 5.14 |
| 9 | 2.7398 | 30.183 | 67.712 | 101.99% | 4.75 |
| 10 | 2.9486 | 33.168 | 69.24 | 101.32% | 4.41 |
| 11 | 3.1673 | 36.284 | 71.042 | 100.88% | 4.10 |
| 12 | 3.3965 | 39.538 | 73.103 | 100.58% | 3.82 |
| 13 | 3.6365 | 42.934 | 75.414 | 100.39% | 3.56 |
| 14 | 3.8876 | 46.48 | 77.968 | 100.27% | 3.33 |
| 15 | 4.1501 | 50.181 | 80.762 | 100.21% | 3.12 |
| 16 | 4.4245 | 54.045 | 83.791 | 100.174% | 2.93 |
| 17 | 4.711 | 58.08 | 87.057 | 100.16% | 2.75 |
| 18 | 5.0102 | 62.291 | 90.558 | 100.17% | 2.59 |

In the table, the column titled "Range" is a measure of the variation in beam diameter as a function of distance in front of the handpiece for the beam produced by a handpiece incorporating the optical system of FIG. 5. The data contained in the Range column indicates how much the spot size varies over a working range of 140 to 260 mm in front of the position of the first surface of lens 28 as a function of the zoom position. The degree of spot size variation is expressed in terms of the percent change in spot size and is calculated by dividing the maximum value of the spot size within the range of 140 to 260 mm by the spot size at 200 mm (the approximate location of the beam waist) and multiplying the result by 100. The data in the column titled "$D_0$" represents the divergence of the beam (in milli-radians) for the beam produced by the optical system which corresponds to the indicated zoom position.

As indicated by the table, at the positions of lenses 30 and 32 corresponding to the smaller spot sizes, optical system 20 provides a beam 26 which changes in size by approximately twenty percent or less over the range of working positions. This change in the beam diameter is due to propagation effects of the inherently Gaussian laser beam which are not altered by the use of aperture 22. At the positions of lenses 30 and 32 corresponding to the moderate to large beam spot sizes, optical system 20 provides a beam 26 having a very long depth of focus, so that the spot size is substantially constant over the range of working distances.

In particular, for spot sizes which vary from 1 to 3 mm in diameter, the data shows that the spot size variation ranges from a maximum of approximately 20% (for a 1.2 mm diameter spot) to a minimum of less than 2% (for a 3 mm diameter spot). For spot sizes which vary from 3 to 5 mm in diameter, the data shows that the spot size variation ranges from a maximum of less than 2% (for a 3 mm diameter spot) to a minimum of less than 0.2% (for a 5 mm diameter spot). The measurements on which the data in the table is based were made with aperture 22 in place.

In the embodiments of the present invention described in this application, the highly collimated output beam is approximately constant in size over the range of working positions shown in FIG. 6. This allows the surgeon to efficiently perform the procedure without concerning themselves with maintaining a fixed distance between the end of the handpiece and the skin surface, thereby permitting the surgeon to concentrate on correctly performing the procedure and not on the movement of the handpiece.

A highly collimated beam assists in performing the type of dermatological procedure for which the handpiece of the present invention is intended to be used by limiting the variation in the energy density of the laser spot as the handpiece is moved over the range of working distances. It is desireable that the energy density vary by no more than approximately 20% for movements of the handpiece over the range of working distances, and it is preferable that it vary by no more than approximately 10%. This corresponds to a desired variation in spot diameter of less than 10%, and a preferred variation of less than 5%.

The laser with which the handpieces of the present invention are intended to be used is the Ultrapulse™ $CO_2$ laser manufactured by Coherent, Inc. Of course, any other laser which is suited for performing dermatological procedures may also be used with the handpieces described in this application. The Ultrapulse™ laser is ideally suited for such procedures because the laser beam is strongly absorbed in the first 10 to 20 microns of depth into the patient's tissue. Owing to the short pulse durations, there is negligible conduction of thermal energy into the underlying tissue. As an example, the Ultrapulse 5000 laser system produces a pulsed infrared laser beam having maximum specifications of 250 millijoules (mj) per pulse, a pulse duration of up to 1 millisecond (ms), and a repetition rate of 400 Hz, for an average power of 100 Watts.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

We claim:

1. A handpiece for transforming an output beam of a laser into a highly collimated resultant beam having an image which is a spot on a patient's skin, comprising:

a handpiece body having an input end and an output end;

an optical system contained in the handpiece body, wherein the optical system includes a zoom lens system capable of producing a focused laser spot of varying sizes, the optical system forming the resultant beam by relaying an image of a beam waist of the laser output beam to a range of working positions, the beam waist being placed substantially at a center of the range of working positions and substantially offset from the output end of the handpiece, the zoom lens system further comprising:

a fixed position diverging lens for forming a virtual image of the beam waist;

a movable position converging lens for relaying the virtual image formed by the fixed position diverging lens to a range of positions from the surface of the diverging lens; and a movable position diverging lens whose position is linked to that of the movable position converging lens so that the position of the movable position diverging lens is maintained at approximately one focal length behind the position of the laser beam waist projected by the movable position converging lens and acts to collimate the beam so that the resultant beam exits the handpiece with a diameter which depends on the positions of the two movable lenses.

2. The handpiece of claim 1, wherein the beam diameter varies by approximately 20% or less over a range of working positions located 140 mm to 260 mm in front of a first surface of the fixed position diverging lens.

3. The handpiece of claim 1, wherein the beam diameter varies by approximately 2% or less over a range of working positions located 140 mm to 260 mm in front of a first surface of the fixed position diverging lens.

4. The handpiece of claim 1, wherein the beam diameter is within the range of 1.5 to 3.0 mm and a beam divergence is less than 10 milli-radians.

5. The handpiece of claim 1, wherein the beam diameter is within the range of 3.0 to 5.0 mm and a beam divergence is less than 5 milli-radians.

6. A handpiece for transforming an output beam of a laser into a highly collimated resultant beam having an image which is a spot on a patient's skin, comprising:

a handpiece body having an input end and an output end;

an aperture placed at the input end of the handpiece body and in front of the laser output beam, the aperture acting to alter a profile of the beam into one which has a substantially uniform energy distribution across its diameter; and an optical system contained in the handpiece body, wherein the optical system includes a zoom lens system capable of producing a focused laser spot of varying sizes, the optical system forming the resultant beam by relaying an image of a beam waist of the laser output beam to a range of working positions, the beam waist being placed substantially at a center of the range of working positions and substantially offset from the output end of the handpiece, the zoom lens system further comprising:

a fixed, position diverging lens for forming a virtual image of the beam waist;

a movable position converging lens for relaying the virtual image formed by the fixed position diverging lens to a range of positions from the surface of the diverging lens; and a movable position diverging lens whose position is linked to that of the movable position converging lens so that the position of the movable position diverging lens is maintained at approximately one focal length behind the position of the laser beam waist projected by the movable position converging lens and acts to collimate the beam so that the resultant beam exits the handpiece with a diameter which depends on the positions of the two movable lenses.

7. The handpiece of claim 6, wherein the beam diameter varies by approximately 20% or less over a range of working positions located 140 mm to 260 mm in front of a first surface of the fixed position diverging lens.

8. The handpiece of claim 6, wherein the beam diameter varies by approximately 2% or less over a range of working positions located 140 mm to 260 mm in front of a first surface of the fixed position diverging lens.

9. The handpiece of claim 6, wherein the beam diameter is within the range of 1.5 to 3.0 mm and a beam divergence is less than 10 milli-radians.

10. The handpiece of claim 6, wherein the beam diameter is within the range of 3.0 to 5.0 mm and a beam divergence is less than 5 milli-radians.

* * * * *